US011089942B2

(12) United States Patent
Kishioka et al.

(10) Patent No.: US 11,089,942 B2
(45) Date of Patent: Aug. 17, 2021

(54) PORTABLE ENDOSCOPE HAVING VIDEO DISPLAY DEVICE OFFSET RELATIVE TO LONGITUDINAL AXIS OF OPERATION PORTION

(71) Applicant: OLYMPUS CORPORATION, Tokyo (JP)

(72) Inventors: Shigeyasu Kishioka, Kunitachi (JP); Yoki Onishi, Hachioji (JP); Masami Shimizu, Hachioji (JP); Tomomi Nakajima, Singapore (SG)

(73) Assignee: OLYMPUS CORPORATION, Tokyo (JP)

( * ) Notice: Subject to any disclaimer, the term of this patent is extended or adjusted under 35 U.S.C. 154(b) by 370 days.

(21) Appl. No.: 16/038,287

(22) Filed: Jul. 18, 2018

(65) Prior Publication Data
US 2018/0317747 A1 Nov. 8, 2018

Related U.S. Application Data

(63) Continuation of application No. PCT/JP2016/078084, filed on Sep. 23, 2016.

(30) Foreign Application Priority Data

Jan. 20, 2016 (JP) .............................. JP2016-008631

(51) Int. Cl.
*A61B 1/00* (2006.01)
*G02B 23/24* (2006.01)
(Continued)

(52) U.S. Cl.
CPC ...... *A61B 1/00048* (2013.01); *A61B 1/00052* (2013.01); *A61B 1/0052* (2013.01);
(Continued)

(58) Field of Classification Search
CPC .................................................. A61B 1/00052
See application file for complete search history.

(56) References Cited

U.S. PATENT DOCUMENTS

2007/0030344 A1* 2/2007 Miyamoto ........... A61B 1/0669
348/65
2007/0188604 A1 8/2007 Miyamoto et al.
(Continued)

FOREIGN PATENT DOCUMENTS

CN 101392873 A 3/2009
EP 1719445 A1 11/2006
(Continued)

OTHER PUBLICATIONS

International Search Report dated Nov. 22, 2016 issued in PCT/JP2016/078084.

*Primary Examiner* — Michael J Carey
*Assistant Examiner* — Minqiao Huang
(74) *Attorney, Agent, or Firm* — Scully, Scott, Murphy & Presser, P.C.

(57) ABSTRACT

A portable endoscope includes: an operation portion; a video display device provided with a display portion and a device body; and a suction valve or a gas feeding adapter including a tube connecting portion provided on a fluid pipe sleeve. The body attaching portion of the device body is provided at a predetermined position positionally displaced from a central part of the device body; and the tube connecting portion is arranged along a back face of the device body and arranged in a display portion projection range projecting outward from the operation portion left side face viewed from the video display screen side.

4 Claims, 4 Drawing Sheets

(51) Int. Cl.
*A61B 1/015* (2006.01)
*A61B 1/04* (2006.01)
*A61B 1/005* (2006.01)

(52) U.S. Cl.
CPC ...... *A61B 1/00066* (2013.01); *G02B 23/2476* (2013.01); *A61B 1/015* (2013.01); *A61B 1/04* (2013.01)

(56) References Cited

U.S. PATENT DOCUMENTS

| | | | | |
|---|---|---|---|---|
| 2007/0249904 A1* | 10/2007 | Amano | ................ | A61B 1/045 600/131 |
| 2008/0009677 A1* | 1/2008 | Shoroji | ............ | A61B 1/00052 600/160 |
| 2008/0021268 A1* | 1/2008 | Shoroji | ............ | A61B 1/00052 600/101 |
| 2009/0036742 A1* | 2/2009 | Watanabe | ............ | A61B 1/042 600/178 |
| 2009/0080214 A1* | 3/2009 | Watanabe | ......... | A61B 1/00052 362/574 |
| 2009/0122574 A1* | 5/2009 | Ogawa | .................... | A61B 1/07 362/574 |
| 2009/0225159 A1* | 9/2009 | Schneider | ......... | A61B 1/00105 348/82 |
| 2010/0095969 A1* | 4/2010 | Schwartz | ........... | A61B 1/00048 128/207.14 |
| 2011/0009694 A1* | 1/2011 | Schultz | ............. | A61B 1/00105 600/109 |
| 2011/0018989 A1 | 1/2011 | Miyamoto et al. | | |
| 2011/0201884 A1* | 8/2011 | Kishioka | ................ | A61B 1/042 600/109 |
| 2011/0208002 A1* | 8/2011 | Kishioka | .............. | A61B 1/0052 600/146 |
| 2011/0313347 A1* | 12/2011 | Zocca | ................ | A61B 1/00052 604/35 |
| 2012/0209065 A1* | 8/2012 | Hosaka | .............. | A61B 1/00066 600/109 |
| 2014/0051923 A1* | 2/2014 | Mirza | ................ | A61B 1/00195 600/103 |
| 2014/0111634 A1* | 4/2014 | Mueckl | ............... | H04N 5/2252 348/82 |
| 2014/0180007 A1* | 6/2014 | Edidin | ............... | A61B 1/00105 600/122 |
| 2015/0150441 A1* | 6/2015 | Ouyang | ................ | A61B 10/04 600/109 |
| 2015/0164313 A1* | 6/2015 | Ouyang | ................... | A61B 1/05 600/103 |
| 2015/0366445 A1* | 12/2015 | Rutgers | ................. | A61B 1/05 600/120 |
| 2016/0331213 A1* | 11/2016 | Kim | ................ | A61B 1/00048 |
| 2016/0374546 A1* | 12/2016 | Berbee | ..................... | A61B 1/05 600/109 |

FOREIGN PATENT DOCUMENTS

| | | |
|---|---|---|
| EP | 1880660 A1 | 1/2008 |
| JP | 2005-192738 A | 7/2005 |
| JP | 2005-192931 A | 7/2005 |
| JP | 2005-237513 A | 9/2005 |
| JP | 2008-043726 A | 2/2008 |
| JP | 2010-227238 A | 10/2010 |
| WO | WO 2005/077252 A1 | 8/2005 |

* cited by examiner

PORTABLE ENDOSCOPE HAVING VIDEO DISPLAY DEVICE OFFSET RELATIVE TO LONGITUDINAL AXIS OF OPERATION PORTION

CROSS REFERENCE TO RELATED APPLICATION

This application is a continuation application of PCT/JP2016/078084 filed on Sep. 23, 2016 and claims benefit of Japanese Application No. 2016-008631 filed in Japan on Jan. 20, 2016, the entire contents of which are incorporated herein by this reference.

BACKGROUND OF THE INVENTION

1. Field of the Invention

The present invention relates to a portable endoscope in which a video display device and a fluid tube are attached to an operation portion.

2. Description of the Related Art

Recently, endoscopes are used in a medical field, an industrial field and the like. Endoscopes include video scopes in which an image pickup apparatus is included in a distal end portion of an insertion portion and fiber scopes in which an image guide including a bundle of optical fibers is inserted inside the insertion portion.

Japanese Patent Application Laid-Open Publication No. 2008-43726 discloses a small-size endoscope apparatus suitable for carrying. The endoscope apparatus is provided with a video display device in an operation portion of a portable endoscope. The operation portion includes a grasping portion to be grasped by a user and an operation portion body provided on a proximal end side of the grasping portion.

As shown in FIG. 1 of Japanese Patent Application Laid-Open Publication No. 2008-43726, an insertion portion including a bending portion extends from a distal end side of the grasping portion. The video display device is fixed to a display device attaching face provided on a top face of the operation portion body such that a video display surface of the display device faces an upper side in FIG. 1.

On a side face located between the top face and a bottom face of the operation portion body, a bending operation lever, a suction pipe sleeve, a ventilation pipe sleeve and the like are provided. The bending operation lever is formed in an L shape, having a finger rest portion and an arm portion. On a front face, which is a side face and faces a front of the user, the finger rest portion is arranged.

An end portion of the arm portion of the bending operation lever is pivotally supported on a right side face located on a right side relative to the front face turnably. Further, the ventilation pipe sleeve is provided projecting from a left side face that is a face opposite to the right side face.

Further, the suction pipe sleeve is provided on an opposite face, which is a face opposite to the front face. The suction pipe sleeve is provided with a suction valve, and a tube connecting portion of the suction valve is extended outward from the left side face side. An elongated suction tube is adapted to be connected to the tube connecting portion.

SUMMARY OF THE INVENTION

A portable endoscope of an aspect of the present invention includes: an operation portion provided with an insertion portion inserted into a subject/object, on a lower part and including an opening portion of a fluid pipe sleeve on a back face that is a face on an opposite side of a front face facing a front of an operator when the operator grasps the operation portion; a video display device including an observation image display portion where an endoscopic image is displayed, wherein the video display device is arranged in a positionally displaced manner so as to project from one side of a right side face side and a left side face side of the operation portion when seen from the front face side in a state of an opposite face of the observation image display portion being arranged on a top portion of the operation portion; a fluid tube connected to a tube connecting portion of an adapter provided on the fluid pipe sleeve and extended to the one side from a back face side of the video display device; and buttons enabling selection of functions, the buttons being arranged in a direction on an opposite side of the one side relative to the observation image display portion.

DETAILED DESCRIPTION OF THE PREFERRED EMBODIMENT

Figure 1:
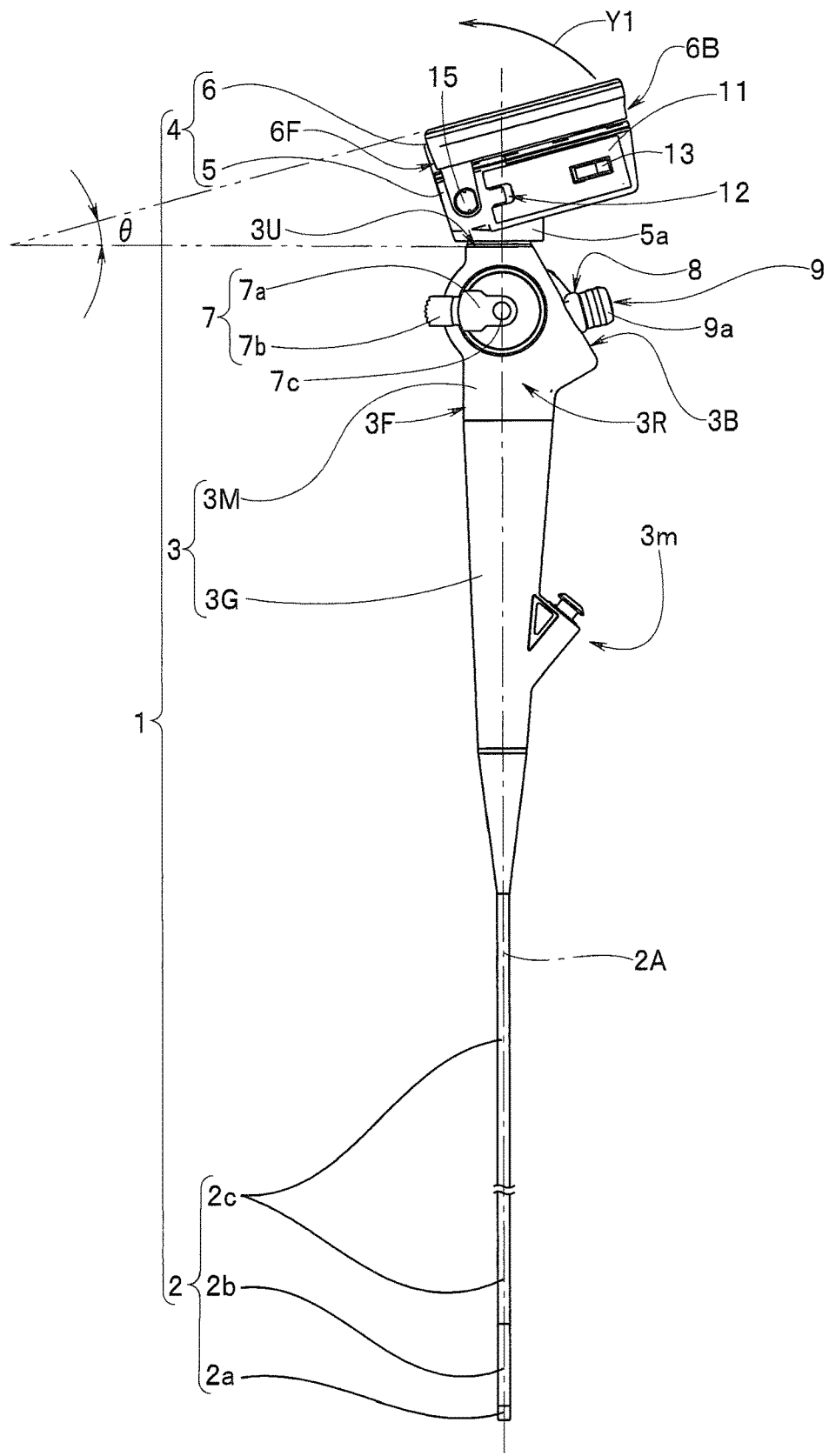
FIG. 1 is a side view illustrating an endoscope provided with a video display device.

An embodiment of the present invention will be described below with reference to drawings.

Note that, on each of the drawings used in the description below, a reduced scale may be caused to be different for each component so that the component is in a size recognizable on the drawing. Further, the present invention is not limited only to the number of components, shapes of the components, a size ratio among the components, and a relative positional relationship among the respective components illustrated on the drawings.

Figure 2:
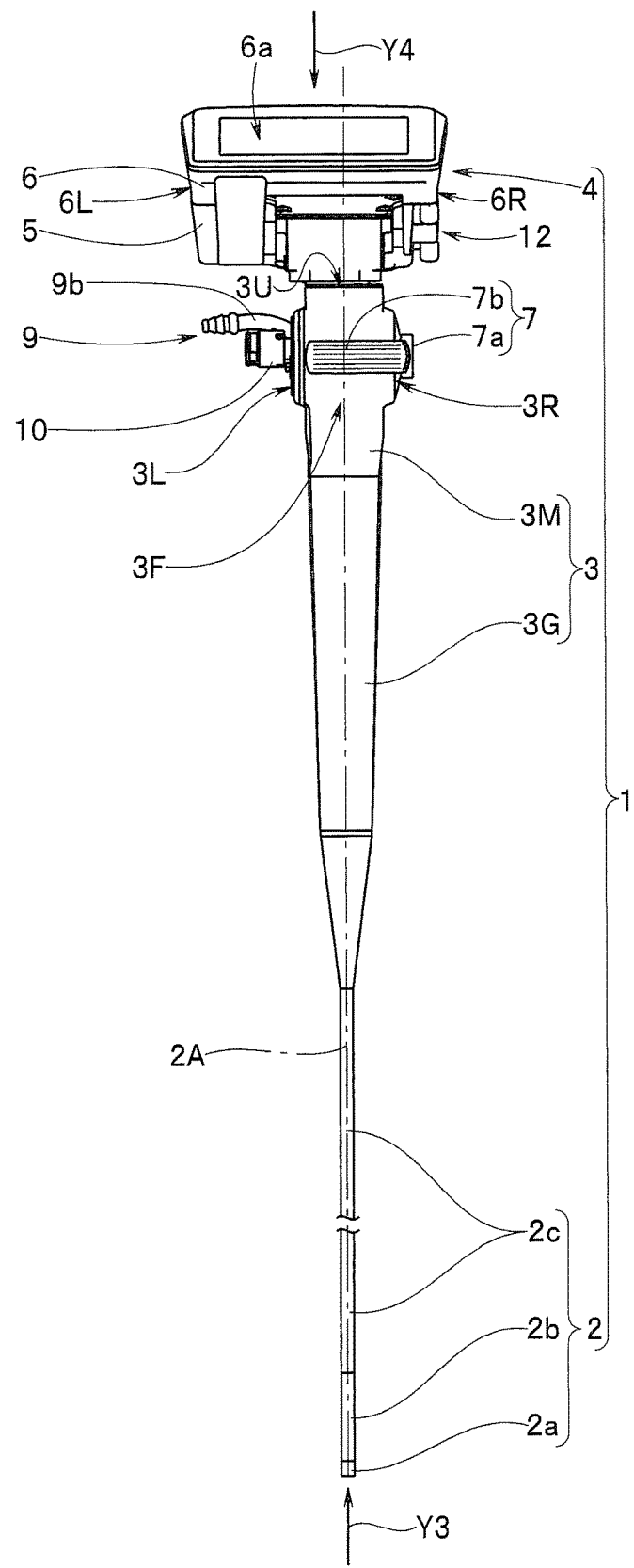
FIG. 2 is a front view illustrating the endoscope provided with the video display device.

As shown in FIGS. 1 and 2, a portable endoscope (hereinafter briefly referred to as an endoscope) 1 is mainly configured being provided with an insertion portion 2, an operation portion 3 and a video display device 4. The operation portion 3 includes an operation portion body 3M and a grasping portion 3G. The video display device 4 includes a device body 5 and a display portion 6. A video display screen 6a of the display portion 6 is in a rectangular shape.

In FIGS. 1 and 2, the insertion portion 2 is in a state of hanging from a bottom face, which is one end of the operation portion 3, in a vertical direction.

The insertion portion 2 includes a distal end portion 2a, a bending portion 2b and a flexible tube portion 2c connectedly arranged from a distal end side in that order. The flexible tube portion 2c is a tube body having flexibility determined in advance. The bending portion 2b is configured to bend, for example, in a vertical direction.

The grasping portion 3G of the operation portion 3 is provided on a proximal end side of the insertion portion 2. The operation portion body 3M is arranged being connected to the grasping portion 3G. A top face 3U corresponding to a top portion on an opposite side of the grasping portion 3G of the operation portion body 3M is a video display device attaching face. The top face 3U is adapted so that a body attaching portion 5a of the video display device 4 is arranged, fitted and fixed.

Figure 3:
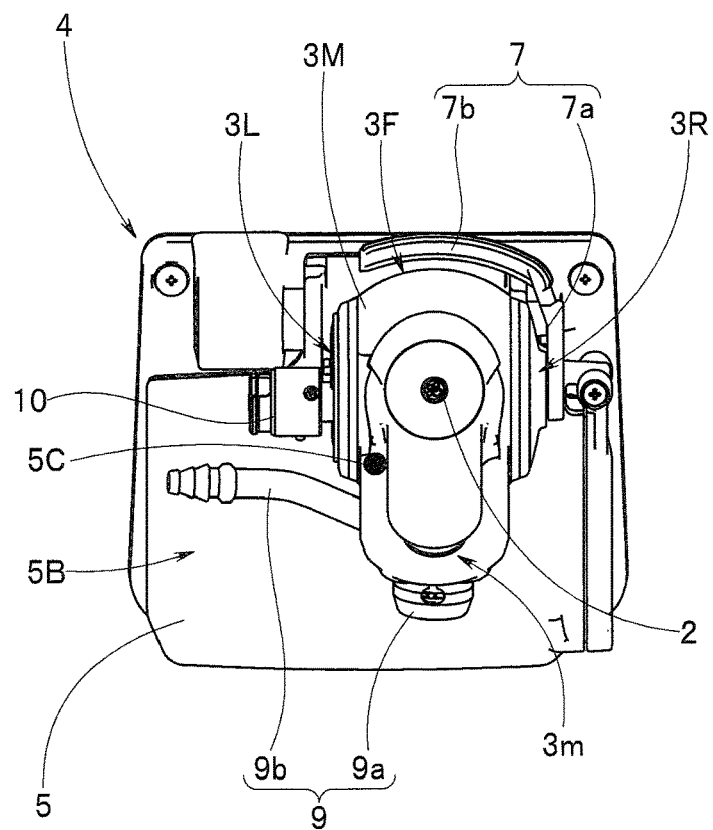
FIG. 3 is a diagram when the portable endoscope is viewed from a direction of an arrow Y3 in FIG. 2.

Reference numerals 3F, 3L, 3R and 3B shown in FIGS. 1 to 3 indicate an operation portion front face, an operation portion left side face, an operation portion right side face and an operation portion back face, respectively, which are provided between the top face 3U and a bottom face of the operation portion body 3M.

The operation portion front face 3F is a face that substantially faces a front of a user, who is an operator, when the user operates a bending operation lever 7 with a finger of a hand grasping the grasping portion 3G.

The bending operation lever 7 includes an arm portion 7a and a finger rest portion 7b and is formed in an L shape. The arm portion 7a is turnably attached to the operation portion right side face 3R with a shaft member 7c, and the finger rest portion 7b is arranged in a manner of moving along a curved surface of a protruding portion of the operation portion front face 3F. As a result, a rotation operation of the finger rest portion 7b of the bending operation lever 7 can be performed by a finger of the user's hand grasping the grasping portion 3G, for example, the thumb.

The bending portion 2b is configured to perform a bending operation in an upward direction or a downward direction by a bending wire (not shown) being pulled or relaxed, accompanying a rotation operation of the bending operation lever 7.

The operation portion back face 3B is a face on an opposite side of the operation portion front face 3F and is, for example, an inclined surface. The operation portion back face 3B is provided with a fluid pipe sleeve 8. On the fluid pipe sleeve 8, for example, a suction button portion 9a of a suction valve 9, which is an adapter, is arranged. The suction valve 9 includes the suction button portion 9a and a tube connecting portion 9b.

Note that there may be a case where the fluid pipe sleeve 8 is provided with a gas feeding adapter including a tube connecting portion (not shown) instead of the suction valve 9. The gas feeding adapter may be provided or may not be provided with a switching button for switching between a gas feeding enabled state and a gas feeding blocked state.

As shown in FIGS. 2 and 3, the tube connecting portion 9b is arranged in a manner of being extended outward from the left side face 3L along a back face 5B that is one face of the device body 5. The elongated tube connecting portion 9b is adapted so that a fluid tube 9c extended from a suction device not shown is connected.

In the case where the fluid pipe sleeve 8 is provided with the gas feeding adapter instead of the suction valve 9, a fluid tube extended from a gas feeding device (not shown) is connected.

Note that reference numeral 3m shown in FIGS. 1 and 3 indicates a treatment instrument insertion opening, which is an introduction opening for inserting an endoscope treatment instrument such as forceps. Reference numeral 10 indicates a ventilation pipe sleeve, which is used at the time of a water leak inspection of an endoscope. The ventilation pipe sleeve 10 is provided in a manner of projecting from the operation portion left side face 3L. The ventilation pipe sleeve 10 is adapted so that a ventilation tube (not shown) extended from a ventilation device not shown is connected.

Reference numeral 11 in FIG. 1 indicates a cover body. The cover body 11 closes an accommodation space opening communicating with an accommodation space (not shown) for accommodating a battery and a recording medium provided in the device body 5. The cover body 11 is turnable relative to the device body 5 via a hinge portion 12 shown in FIGS. 1 and 2.

Further, reference numeral 13 shown in FIG. 1 indicates a slide button. The cover body 11 is adapted to be switched to a closed state or an openable state by causing an arrangement position of the slide button 13 to change.

As shown in FIGS. 1 and 2, the device body 5 of the video display device 4 includes the body attaching portion 5a. One face of the body attaching portion 5a is adapted to be arranged on the top face 3U of the operation portion 3 and integrally attached and fixed.

In the fixed state, a video display screen (hereinafter briefly referred to as a display screen) 6a of the display portion 6 is arranged being inclined at a predetermined angle θ relative to horizontality so as to face the front of the user.

The display portion 6 is in a flat rectangular parallelepiped shape and is pivotally supported by a rotation axis member 15 relative to the device body 5 turnably. As shown in FIG. 1, the display portion 6 is generally arranged at a position of being in substantially close contact with the device body 5. The display portion 6 is adapted so as to be rotated as necessary as shown by an arrow Y1 with the rotation axis member 15 as a center. That is, the display screen 6a inclined at the angle θ can be further inclined and changed to a direction desired by the user.

As shown in FIG. 3, the body attaching portion 5a is provided in a positionally displaced manner from a central portion 5c of the device body 5. Therefore, when the video display device 4 is attached and fixed to the operation portion 3, the video display device 4 is positionally displaced to a back face side relative to a longitudinal axis 2A as shown in FIG. 1 and is positionally displaced to a left side relative to the longitudinal axis 2A as shown in FIG. 2.

More specifically, while a left side face 6L of the display portion 6 constituting the video display device 4 significantly projects outward from the operation portion left side face 3L, a right side face 6R of the display portion 6 slightly projects outward from the operation portion right side face 3R. Further, a front face 6F of the display portion 6 constituting the video display device 4 slightly projects outward from the operation portion front face 3F, and a back face 6B of the display portion 6 significantly projects from the operation portion back face 3B.

Figure 4:
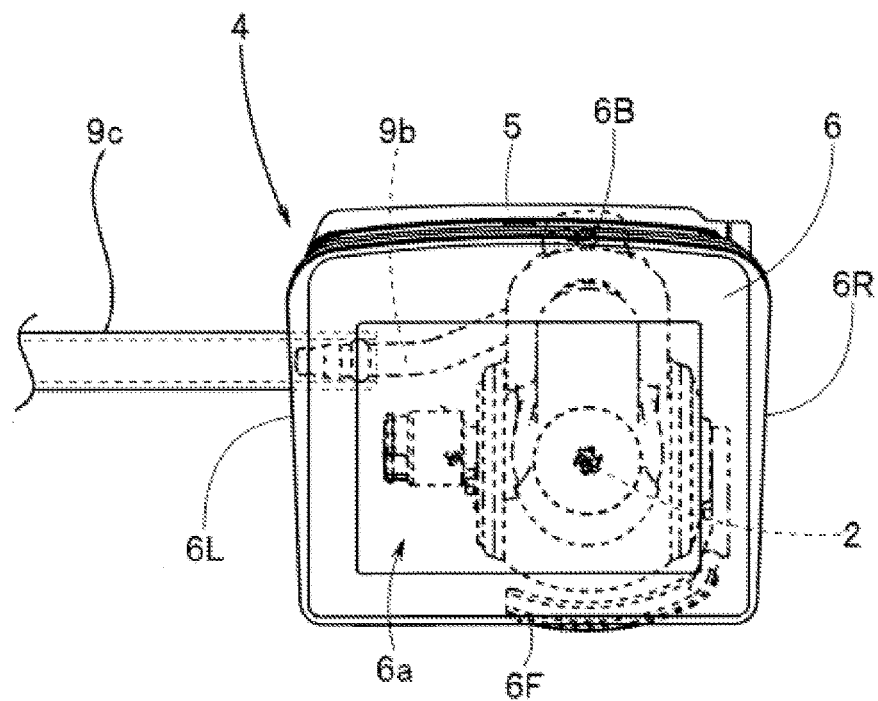
FIG. 4 is a diagram when the portable endoscope is viewed from a direction of an arrow Y4 in FIG. 2.

When the video display screen 6a of the display portion 6 is viewed from above as shown by an arrow Y4A in FIG. 2, the tube connecting portion 9b of the suction valve 9 is arranged in a projection range of the video display device 4 as shown in FIG. 4.

Note that, in the above description, it is assumed that the tube connecting portion 9b of the suction valve 9 is arranged in the projection range of the video display device 4. However, the tube connecting portion 9b may be arranged projecting to the left side face 6L side from an inside of the projection range of the video display device 4.

Therefore, in a state in which the fluid tube 9c is connected to the tube connecting portion 9b as shown by a two-dot chain line in FIG. 4, the fluid tube 9c extends outward from the left side face 6L side of the display portion 6 as shown in FIG. 4.

Thus, in order that the video display device 4 is caused to be positionally displaced to the operation portion left side face 3L side, and the fluid tube 9c is led in an outward direction from the operation portion left side face 3L, the same direction as the positional displacement direction, from the back face side of the video display device 4, the tube connecting portion 9b of the suction valve 9 is arranged in the projection range, along the back face 5B of the device body 5 constituting the video display device 4.

As a result, the operation portion right side face 3R side on an opposite side of the operation portion left side face 3L becomes open when the user grasps the grasping portion 3G of the operation portion 3 with his left hand to perform an operation. Therefore, a problem that a field of vision is obstructed and a problem that a right hand grasping the insertion portion 2 interferes with a suction tube are solved, and the user can smoothly and certainly perform a procedure.

In the embodiment described above, it is assumed that the user grasps the grasping portion 3G of the operation portion 3 with his left hand. In a case where the user grasps the grasping portion 3G of the operation portion 3 with his right hand, however, the video display device 4 is caused to be positionally displaced to the operation portion right side face 3R side, and, then, the tube connecting portion 9b of the suction valve 9 is arranged in the projection range on the back face 5B side of the device body 5, along the back face 5B, contrary to the configuration described above.

Thereby, when the user grasps the grasping portion 3G of the operation portion 3 with his right hand to perform an operation, the operation portion right side face 3R side becomes open, and it is possible to obtain operation and an effect similar to the above description.

Note that it is also possible to make the positional displacement direction of the video display device 4 a direction to the operation portion back face 3B side, and arrange the tube connecting portion 9b of the suction valve 9 in the projection range on the back face 5B side of the device body 5, along the back face 5B.

Here, the video display screen 6a of the display portion 6 will be described.

Figure 5:
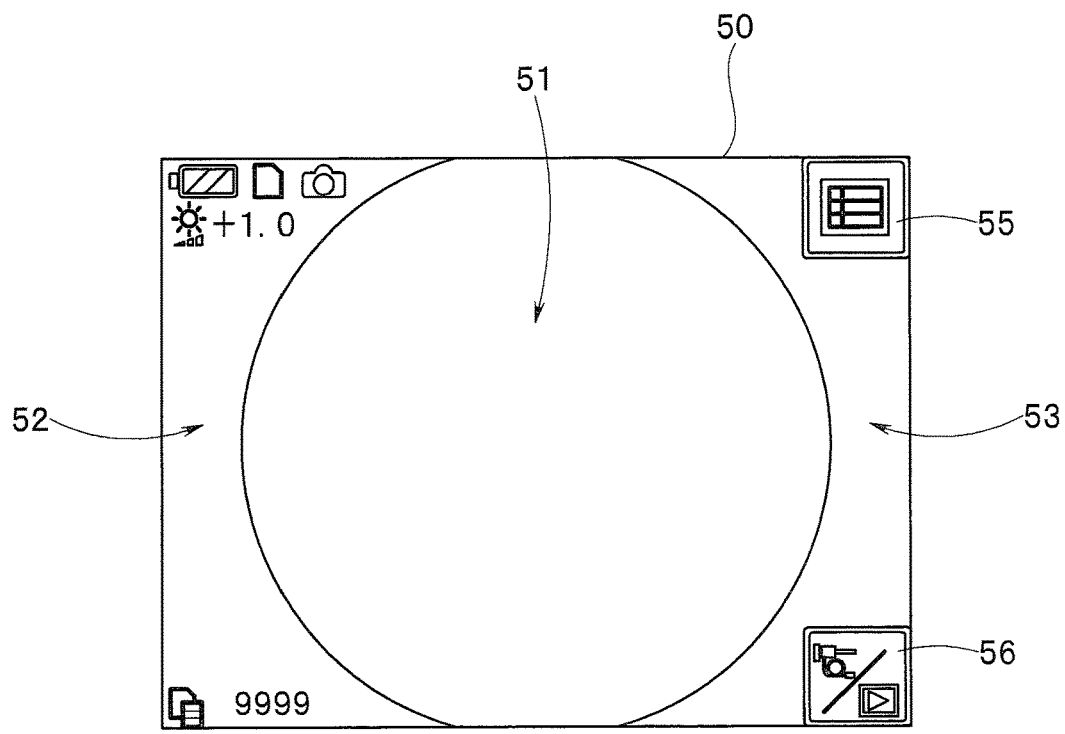
FIG. 5 is a diagram illustrating an initial screen at startup.

When a startup switch of the endoscope 1 is turned on, an initial screen at startup 50 is displayed on the video display screen 6a shown in FIG. 5.

The initial screen at startup 50 includes a substantially circular observation image display portion 51 located at a center, a display area 52 which is a part of a dark color portion around the display portion 51 and is located on a left side of the display portion 51, and a display operation area 53 located on a right side of the display portion 51.

Note that, though the observation image display portion 51 is in a circular shape a part of which is missing as shown in FIG. 5, a display portion in a circular shape with no missing parts is also possible.

In the observation image display portion 51, an endoscopic image captured by the endoscope 1 is displayed.

In the display area 52, various photographing conditions and the like at the time of observation are displayed.

In comparison, the display operation area 53 is according to so-called touch panel specifications and is adapted so that various function buttons are displayed, and the user can touch a button to select a function of the button.

As the function buttons, for example, a menu item selection button 55 on an upper side in FIG. 5 and an observation/function-button-viewing switching button 56 on a lower side in FIG. 5 are given.

Figure 6:
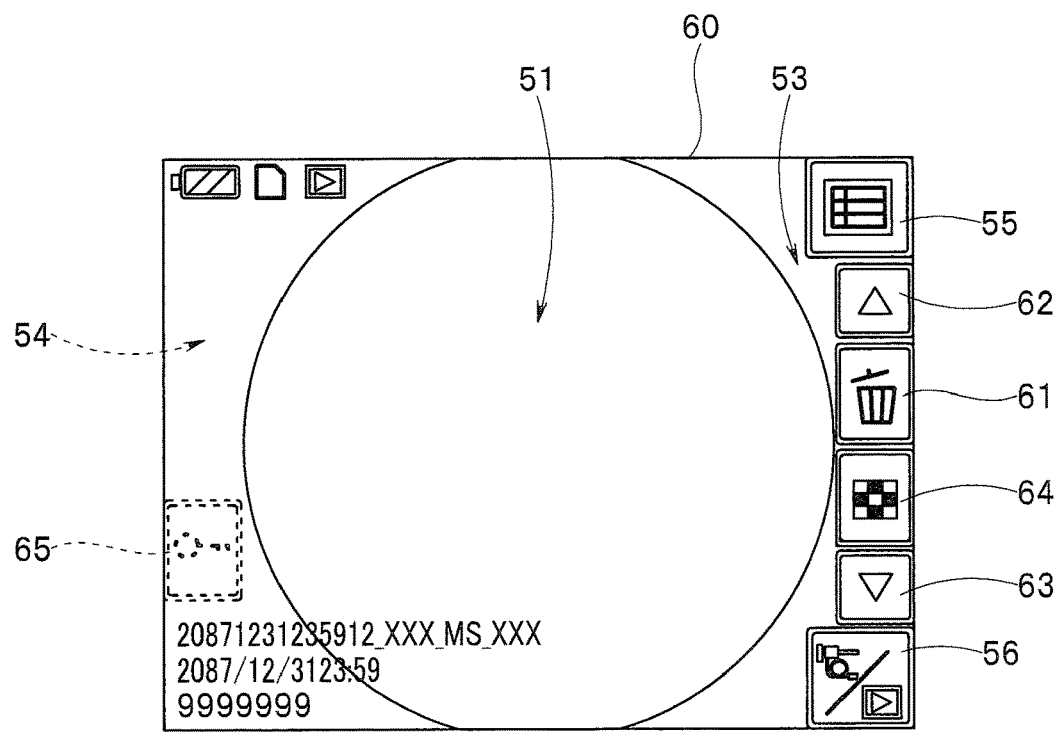
FIG. 6 is a diagram illustrating a function-button-viewing image screen.

When the user selects the observation/function-button-viewing switching button 56 on the initial screen at startup 50, the initial screen at startup 50 switches to a function-button-viewing image screen 60 shown in FIG. 6.

On the function-button-viewing image screen 60, various function buttons such as an image deletion button indicated by reference numeral 61, a function-button-viewing image switching buttons indicated by reference numerals 62 and 63 and a button for switching the number of function-button-viewing images to be displayed which is indicated by reference numeral 64 are displayed in addition to the menu item selection button 55 and the observation/function-button-viewing switching button 56 described above.

That is, the function buttons 55, 56, 61, 62, 63 and 64 are arranged in the display operation area 53 provided on a right side of the observation image display portion 51 of the video display screen 6a.

The user grasps the grasping portion 3G with his left hand. Therefore, the user performs a pressing operation of the function buttons 55, 56, 61, 62, 63 and 64 with a finger of his right hand. In a state in which the user grasps the grasping portion 3G, a center of gravity of the operation portion 3 exists on a left side because the video display device 4 is positionally displaced to the left side relative to the longitudinal axis 2A as shown in FIG. 2.

As a result, when the user operates any of the function buttons 55, 56, 61, 62, 63 and 64 provided on the right side of the observation image display portion 51 of the video display screen 6a, a force offsetting moment works on the operation portion 3.

Therefore, the user can stably operate the function button.

Then, when the user selects the observation/function-button-viewing switching button 56 on the function-button-viewing image screen 60, the function-button-viewing image screen 60 switches to the initial screen at startup 50 again.

Note that, though the display operation area 53 is according to the touch panel specifications in the embodiment described above, the whole display screen 6a may be according to the touch panel specifications. Further, on the function-button-viewing image screen 60, the display area 52 described above may be a display operation area 54. In this case, function switches that are not often used, for example, an image lock button 65 indicated by broken lines and the like can be provided in the display operation area 54.

Note that the present invention is not limited to the embodiment described above, but various modifications can be practiced in a range not departing from the spirit of the invention.

According to the present invention, it is possible to realize a portable endoscope making it possible to smoothly and certainly perform in a procedure without workability being damaged by a video display device and a fluid tube.

What is claimed is:

1. A portable endoscope comprising:
    an operation portion having a distal end, a proximal end, a front surface, a back surface, a first side surface and a second side surface, the distal end being arranged on an insertion portion configured to be inserted into a subject/object, the operation portion including an opening of a fluid pipe sleeve on the back surface of the operation portion, the back surface being on an opposite side of the front surface, the front surface facing a front of an operator when the operator grasps the operation portion;
    a video display device comprising an observation image display configured to display an endoscopic image, a distal surface of the video display device is arranged on the proximal end of the operation portion, the distal surface of the video display device being opposite to a proximal surface of the video display device on which the observation image display is arranged, wherein the video display device is arranged such that a first side surface of the video display device projects further past the first side surface of the operation portion than a second side surface of the video display device projects from the second side surface of the operation portion, wherein the first side surface of the operation portion is on a same side surface as the first side surface of the video display device and the second side surface of the operation portion is on a same side surface as the second side surface of the video display device;

a fluid tube connected to a tube connecting portion of an adapter provided on the fluid pipe sleeve, the fluid tube extending towards the first side surface of the video display device along the distal surface of the video display device; and buttons enabling selection of functions, the buttons being arranged on the proximal surface of the video display device between the second side surface of the operation portion and the second side surface of the video display device.

2. The portable endoscope according to claim 1, wherein the adapter is a suction valve or a gas feeding adapter.

3. The portable endoscope according to claim 1, wherein the insertion portion comprises a bending portion and the operation portion further comprises a lever operatively connected to the bending portion, the lever having a finger contact surface, moving the finger contact surface relative to the operation portion bends the bending portion, the finger contact portion being movably disposed on the front surface of the operation portion.

4. The portable endoscope according to claim 3, wherein a back surface of the video display device projects further past the back surface of the operation portion than a front surface of the video display device projects from the front surface of the operation portion.

* * * * *